United States Patent [19]

Rovnyak

[11] 4,003,890
[45] Jan. 18, 1977

[54] BENZYLIDENE PYRANO[4,3-c]PYRAZOLES

[75] Inventor: George C. Rovnyak, Hopewell, N.J.

[73] Assignee: E. R. Squibb & Sons, Inc., Princeton, N.J.

[22] Filed: May 27, 1976

[21] Appl. No.: 690,702

[52] U.S. Cl. .......................................... 260/240 F
[51] Int. Cl.² .............. C07D 491/06; C07D 405/12
[58] Field of Search .................... 260/240 F, 310 R

[56] References Cited

UNITED STATES PATENTS

| 3,624,102 | 11/1971 | Brown et al. | 260/310 R |
|---|---|---|---|
| 3,852,279 | 12/1974 | Krapcho et al. | 260/240 F |
| 3,897,420 | 7/1975 | Krapcho et al. | 260/240 F |
| 3,962,222 | 6/1976 | Krapcho et al. | 260/240 F |

OTHER PUBLICATIONS

Chem. Abs. 28,756q, vol. 77, 1972 p. 10.

*Primary Examiner*—Allen B. Curtis
*Attorney, Agent, or Firm*—Lawrence S. Levinson; Merle J. Smith; Donald J. Barrack

[57] ABSTRACT

Compounds having the formula

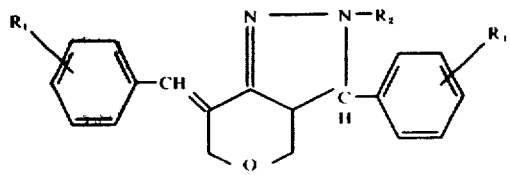

wherein $R_1$ is hydrogen, hydroxy, alkyl, alkoxy, alkylthio, trifluoromethyl, halogen, nitro, cyano, dialkylamino or alkylsulfinyl; and $R_2$ is hydrogen, alkyl, aryl, arylalkyl, acyl or an aminoalkylene have useful antiinflammatory activity.

6 Claims, No Drawings

BENZYLIDENE PYRANO[4,3-C]PYRAZOLES

BRIEF DESCRIPTION OF THE INVENTION

Pyrano [4,3-c]pyrazoles having the formula

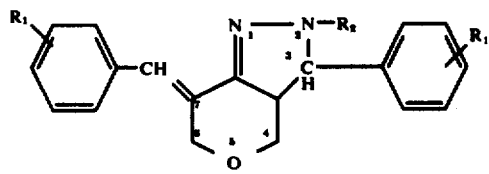

and the pharmaceutically acceptable salts thereof, have useful antiinflammatory activity. In formula I, and throughout the specification, the symbols are as defined below.

$R_1$ can be hydrogen, hydroxy, alkyl, alkoxy, alkylthio, trifluoromethyl, halogen, nitro, cyano, dialkylamino or alkylsulfinyl; and $R_2$ can be hydrogen, alkyl, aryl, arylalkyl,

wherein X is alkyl or aryl, or $A\text{-}NR_3R_4$ wherein A is a straight or branched chain alkylene group having 2 to 5 carbon atoms, $R_3$ can be hydrogen or alkyl, and $R_4$ can be hydrogen, alkyl, phenyl or phenylalkyl, or $R_3$ and $R_4$ together with the nitrogen atom to which they are attached can be

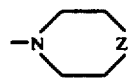

wherein Z can be $CH_2$, oxygen or $N\text{-}R_5$ wherein $R_5$ can be hydrogen, alkyl, aryl or arylalkyl.

The terms "alkyl" and "alkoxy" as used throughout the specification (individually or as part of a larger group) refer to groups having 1 to 8 carbon atoms; alkyl and alkoxy groups having 1 to 3 carbon atoms are preferred.

The term "halogen" as used throughout the specification refers to fluorine, chlorine, bromine and iodine; fluorine and chlorine are preferred.

The term "aryl" as used throughout the specification (individually or as part of a larger group) refers to phenyl or phenyl monosubstituted with an alkyl, alkoxy, halogen or trifluoromethyl group; phenyl is preferred.

DETAILED DESCRIPTION OF THE INVENTION

The compounds of formula I are prepared using as starting materials a substituted tetrahydro-4H-pyran-4-one having the formula

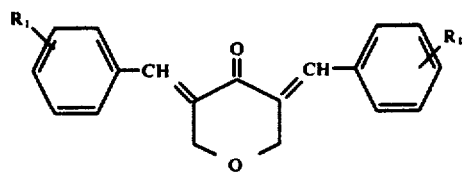

and a hydrazine having the formula

The compounds of formulas II and III are readily obtainable; see, for example, Journal of the American Chemical Society, 79:156 (1957) and Journal of Medicinal Chemistry, 7:493 (1964).

A substituted tetrahydro-4H-pyran-4-one of formula II can be prepared by reacting tetrahydro-4H-pyran-4-one with an appropriate benzaldehyde having the formula

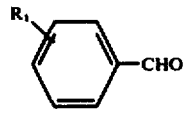

A hydrazine of formula III can be prepared by reacting an excess of hydrazine ($H_2NNH_2$) with a compound having the formula

wherein Y is chlorine or bromine.

Reaction of a substituted tetrahydro-4H-pyran-4-one of formula II with a hydrazine of formula III yields a product of formula I. The reaction can be run in an organic solvent, preferably a lower alkanol such as methanol. While reaction conditions are not critical, the reaction will preferably be run at, or near, the reflux temperature of the solvent.

Alternatively, compounds of formula I wherein $R_2$ is hydrogen can be used as intermediates for the preparation of other compounds of formula I, by reaction with alkylating and acylating agents using procedures well known in the art.

Still another method for preparing the compounds of formula I wherein $R_2$ is $A\text{-}NR_3R_4$ comprises first reacting a substituted tetrahydro-4H-pyran-4-one of formula II with a hydroxyalkyl hydrazine having the formula

to form an intermediate having the formula

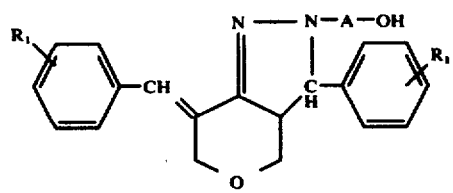

An alcohol of formula VII can be reacted with an alkylsulfonyl or arylsulfonyl halide, preferably p-toluenesulfonyl halide, to yield a compound of the formula

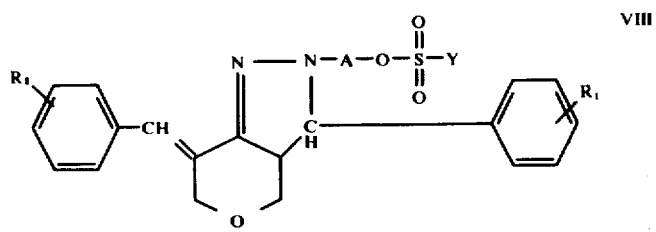

wherein Y is alkyl or aryl. The intermediate of formula VIII can be treated with a compound having the formula

HNR₃R₄    IX.

to yield the products of formula I. This method is particularly useful in preparing those compounds of formula I wherein R₂ is A-NR₃R₄, and R₃ and R₄ are both hydrogen.

The compounds of formula I wherein R₂ is aminoalkylene form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, oxalate, benzoate, ascorbate, salicylate, methanesulfonate, benzenesulfonate, toluenesulfonate and the like.

The compounds of formula I, and the pharmaceutically acceptable acid addition salts thereof, are useful in treating inflammation in mammalian species, e.g., rats, dogs, cats, monkeys, etc. Joint tenderness and stiffness (in conditions such as rheumatoid arthritis) are relieved by the above described compounds.

The compounds of this invention can be formulated for use as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70kg/day to 2 g/70kg/day, preferably 100 mg/70kg/day to 1 g/70kg/day.

The following examples are specific embodiments of this invention.

EXAMPLE 1

2,3,3a,4,6,7-Hexahydro-3-phenyl-7-(phenylmethylene)-2-propylpyrano[4,3-c]pyrazole A mixture of 3.6g of tetrahydro-3,5-bis-(phenylmethylene)-4H-pyran-4-one and 1.1g of n-propylhydrazine in 250 ml of methanol is heated at reflux temperature for 3 to 4 hours. Methanol is removed in vacuo, and the residue is dissolved in chloroform. The chloroform solution is washed with dilute hydrochloric acid and water. The organic layer is then dried over anhydrous magnesium sulfate and concentrated in vacuo to give 4g of a crude oil. This is triturated with about 10 ml of acetonitrile and left at room temperature overnight. Some crystals precipitate out and are collected by filtration. The filtrate is concentrated and applied to a dry packed alumina column (neutral, activity I). The fractions eluted with hexane are combined with the crystals obtained above and recrystallized from ether/hexane to yield the title compound, melting point 113.5°–115° C.

EXAMPLES 2–22

Following the procedure of Example 1, but substituting the compound listed in column I for tetrahydro-3,5-bis-(phenylmethylene)-4H-pyran-4-one and the compound listed in column II for n-propylhydrazine, yields the compound listed in column III.

| Example | Column I | Column II | Column III |
| --- | --- | --- | --- |
| 2 | tetrahydro-3,5-bis-[(4-methylphenyl)methylene]-4H-pyran-4-one | benzylhydrazine | 3-(4-methylphenyl)-7-[(4-methylphenyl)methylene]-2-benzyl-2,3,3a,4,6,7-hexahydropyrano[4,3-c]pyrazole |
| 3 | tetrahydro-3,5-bis-[(4-cyanophenyl)methylene]-4H-pyran-4-one | ethylhydrazine | 3-(4-cyanophenyl)-7-[(4-cyanophenyl)methylene]-2-ethyl-2,3,3a,4,6,7-hexahydropyrano[4,3-c]pyrazole |
| 4 | tetrahydro-3,5-bis-[(4-nitrophenyl)methylene]-4H-pyran-4-one | n-octylhydrazine | 2,3,3a,4,6,7-hexahydro-3-(4-nitrophenyl)-7-[(4-nitrophenyl)methylene]-2-octyl-pyrano[4,3-c]pyrazole |
| 5 | tetrahydro-3,5-bis-[[4-(dimethylamino)phenyl]methylene]-4H-pyran-4-one | phenylhydrazine | 3-[4-(dimethylamino)phenyl]-7-[[4-(dimethylamino)phenyl]methylene]-2,3,3a,4,6,7-hexahydro-2-phenylpyrano[4,3-c]pyrazole |
| 6 | tetrahydro-3,5-bis-[(3-hydroxyphenyl)methylene]-4H-pyran-4-one | ethylhydrazine | 2-ethyl-2,3,3a,4,6,7-hexahydro-3-(3-hydroxyphenyl)-7-[(3-hydroxyphenyl)methylene]-pyrano[4,3-c]pyrazole |
| 7 | tetrahydro-3,5-bis-[(4-methylthiophenyl)methylene]-4H-pyran-4-one | benzylhydrazine | 2-benzyl-2,3,3a,4,6,7-hexahydro-3-(4-methylthiophenyl)-7-[(4-methylthiophenyl)methylene]-pyrano[4,3-c]pyrazole |
| 8 | tetrahydro-3,5-bis-[(4-ethylsulfinylphenyl)methylene]-4H-pyran-4-one | phenylhydrazine | 3-(4-ethylsulfinylphenyl)-7-[(4-ethylsulfinylphenyl)methylene]-2,3,3a,4,6,7-hexahydro-2-phenylpyrano[4,3-c]pyrazole |
| 9 | tetrahydro-3,5-bis-[(2-methylphenyl)methylene]-4H-pyran-4-one | methylaminopropylhydrazine | 3a,4,6,7-tetrahydro-N-methyl-3-(2-methylphenyl)-7-[(2-methylphenyl)methylene]pyrano[4,3-c]pyrazole-2(3H)-propanamine |

-continued

| Example | Column I | Column II | Column III |
|---|---|---|---|
| 10 | tetrahydro-3,5-bis-[(4-methoxyphenyl)methylene]-4H-pyran-4-one | N-benzyl-N-methyl-aminoethylhydrazine | 3a,4,6,7-tetrahydro-N-benzyl-N-methyl-3-(4-methoxyphenyl)-7-[(4-methoxyphenyl)methylene]pyrano[4,3-c]pyrazole-2(3H)-ethanamine |
| 11 | tetrahydro-3,5-bis-[(4-trifluoromethylphenyl)methylene]-4H-pyran-4-one | N-methyl-N-phenyl-aminopentylhydrazine | 3a,4,6,7-tetrahydro-N-methyl-N-phenyl-3-(4-trifluoromethylphenyl)-7-[(4-trifluoromethylphenyl)methylene]pyrano[4,3-c]pyrazole-2(3H)-pentanamine |
| 12 | tetrahydro-3,5-bis-[(2-chlorophenyl)methylene]-4H-pyran-4-one | (2-aminoethyl)hydrazine | 3a,4,6,7-tetrahydro-3-(2-chlorophenyl)-7-[2-(chlorophenyl)methylene]-pyrano[4,3-c]pyrazole-2(3H)-ethanamine |
| 13 | tetrahydro-3,5-bis-(phenylmethylene)-4H-pyran-4-one | phenylaminopropyl-hydrazine | 3a,4,6,7-tetrahydro-N-phenyl-3-phenyl-7-(phenylmethylene)pyrano[4,3-c]pyrazole-2(3H)-propanamine |
| 14 | tetrahydro-3,5-bis-(phenylmethylene)-4H-pyran-4-one | benzylaminopropyl-hydrazine | 3a,4,6,7-tetrahydro-N-benzyl-3-phenyl-7-(phenylmethylene)pyrano[4,3-c]pyrazole-2(3H)-propanamine |
| 15 | tetrahydro-3,5-bis-[(4-propoxyphenyl)methylene]-4H-pyran-4-one | 3-(dimethylamino)-2-methyl-propyl-hydrazine | 3a,4,6,7-tetrahydro-N,N,β-trimethyl-3-(4-propoxyphenyl)-7-[(4-propoxyphenyl)methylene]pyrano[4,3-c]pyrazole-2(3H)-propanamine |
| 16 | tetrahydro-3,5-bis-(phenylmethylene)-4H-pyran-4-one | 3-(4-methyl-1-piperazinyl)propylhydrazine | 2,3,3a,4,6,7-hexahydro-2-[3-(4-methyl-1-piperazinyl)propyl]-3-phenyl-7-(phenylmethylene)pyrano[4,3-c]pyrazole; melting point 101-104° C; melting point of dimaleate salt 173-175° C |
| 17 | tetrahydro-3,5-bis-[(4-methylsulfinyl)phenylmethylene]-4H-pyran-4-one pyran-4-one | 3-(4-methyl-1-piperazinyl)propylhydrazine | 2,3,3a,4,6,7-hexahydro-2-[3-(4-methyl-1-piperazinyl)propyl]-3-[4-(methylsulfinyl)phenyl]-7-[4-[4-(methylsulfinyl)phenyl]-7-[4-(methylsulfinyl)phenylmethylene]-pyrano[4,3-c]pyrazole; melting point of dimaleate salt 172-174° C |
| 18 | tetrahydro-3,5-bis-(phenylmethylene)-4H-pyran-4-one | 2-(1-piperazinyl)ethyl-hydrazine | 2,3,3a,4,6,7-hexahydro-2-[2-(1-piperazinyl)ethyl]-3-phenyl-7-(phenylmethylene)pyrano[4,3-c]-pyrazole |
| 19 | tetrahydro-3,5-bis-(phenylmethylene)-4H-pyran-4-one | 3-(4-phenyl-1-piperazinyl)propylhydrazine | 2,3,3a,4,6,7-hexahydro-2-[3-(4-phenyl-1-piperazinyl)propyl]-3-phenyl-7-(phenylmethylene)pyrano-[4,3-c]pyrazole |
| 20 | tetrahydro-3,5-bis-(phenylmethylene-4H-pyran-4-one | 4-(4-phenylmethyl-1-piperazinyl)butylhydrazine | 2,3,3a,4,6,7-hexahydro-2-[4-(4-phenylmethyl-1-piperazinyl)butyl]-3-phenyl-7-(phenylmethylene)pyrano-[4,3-c]pyrazole |
| 21 | tetrahydro-3,5-bis-(2-methylphenyl)methylene]-4H-pyran-4-one | 3-(4-morpholinyl)propyl-hydrazine | 2,3,3a,4,6,7-hexahydro-2-[3-(4-morpholinyl)propyl]-3-(2-methylphenyl)-7-[(2-methylphenyl)methylene]-pyrano[4,3-c]pyrazole |
| 22 | tetrahydro-3,5-bis-(phenylmethylene)-4H-pyran-4-one | 2-(1-piperidinyl)ethyl-hydrazine | 2,3,3a,4,6,7-hexahydro-2-[2-(1-piperidinyl)ethyl]-3-phenyl-7-(phenylmethylene)pyrano[4,3-c]pyrazole |

What is claimed is:

1. A compound having the formula

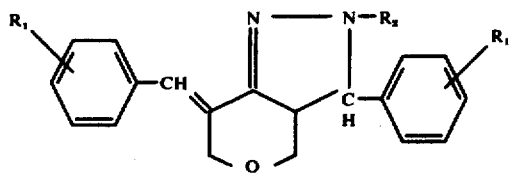

or a pharmaceutically acceptable salt thereof, wherein $R_1$ is hydrogen, hydroxy, alkyl, alkoxy, alkylthio, trifluoromethyl, halogen, nitro, cyano, dialkylamino or alkylsulfinyl; and $R_2$ is hydrogen, alkyl, aryl, arylalkyl,

wherein X is alkyl or aryl, or $A-NR_3R_4$ wherein A is a straight or branched chain alkylene group having 2 to 5 carbon atoms, $R_3$ is hydrogen or alkyl, and $R_4$ is hydrogen, alkyl, phenyl or phenylalkyl, or $R_3$ and $R_4$ together with the nitrogen atom to which they are attached are

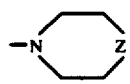

wherein Z is $CH_2$, oxygen or $N-R_5$ wherein $R_5$ is hydrogen, alkyl, aryl or arylalkyl; wherein the terms alkyl and alkoxy refer to groups having 1 to 8 carbon atoms and the term aryl refers to phenyl or phenyl monosubstituted with an alkyl, alkoxy, halogen or trifluoromethyl group.

2. A compound in accordance with claim 1 wherein $R_2$ is hydrogen, alkyl, aryl, arylalkyl, or X-C- wherein X is alkyl or aryl.

3. A compound in accordance with claim 1 wherein $R_2$ is $A-NR_3R_4$.

4. A compound in accordance with claim 3 wherein $R_3$ is hydrogen or alkyl and $R_4$ is hydrogen, alkyl, phenyl or phenylalkyl.

5. A compound in accordance with claim 3 wherein $NR_3R_4$ is

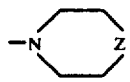

6. A compound in accordance with claim 5 wherein Z is $N-R_5$.

* * * * *

UNITED STATES PATENT AND TRADEMARK OFFICE
CERTIFICATE OF CORRECTION

PATENT NO. : 4,003,890
DATED : January 18, 1977
INVENTOR(S) : George C. Rovnyak

It is certified that error appears in the above-identified patent and that said Letters Patent are hereby corrected as shown below:

Column 6, line 52, "X-C-" should read:

$$-- X-\overset{\overset{O}{\|}}{C}- --.$$

Signed and Sealed this

Fifth Day of April 1977

[SEAL]

Attest:

RUTH C. MASON
*Attesting Officer*

C. MARSHALL DANN
*Commissioner of Patents and Trademarks*